United States Patent [19]

Sakata et al.

[11] Patent Number: 4,462,994
[45] Date of Patent: Jul. 31, 1984

[54] N-CONTAINING HETEROCYCLIC RING-SUBSTITUTED O-ARYLPHOSPHATE DERIVATIVES, PREPARATION THEREOF, AND INSECTICIDES, ACARICIDES AND NEMATOCIDES CONTAINING SAID DERIVATIVES

[75] Inventors: Gojyo Sakata; Tatsuo Numata; Kazuya Kusano, all of Funabashi; Masayoshi Hirose; Kiminori Hirata, both of Minami Saitama, all of Japan

[73] Assignee: Nissan Chemical Industries, Inc., Tokyo, Japan

[21] Appl. No.: 376,639

[22] Filed: May 10, 1982

[30] Foreign Application Priority Data

May 19, 1981 [JP] Japan ................................. 56-75149
Nov. 26, 1981 [JP] Japan ................................ 56-189680

[51] Int. Cl.³ ............................................... C07F 9/18
[52] U.S. Cl. ................................... 424/200; 424/250; 544/337
[58] Field of Search .................... 544/337; 424/250 F, 424/200; 546/21, 23, 25

[56] References Cited

U.S. PATENT DOCUMENTS 3,225,044 12/1965 Dauterman et al. ............... 544/337
3,320,261  5/1967 Lorenz et al. ..................... 546/23
3,432,503  3/1969 Ferguson .......................... 544/337
3,763,160 10/1973 Schmidt et al. .................... 544/337
3,929,998 12/1975 Lovell .............................. 424/200
3,954,755  5/1976 Schmidt et al. .................... 544/337
4,056,581 11/1977 Bayer et al. ....................... 260/972
4,080,443  3/1978 Malhotra .......................... 424/200
4,096,210  6/1978 Freedman et al. ................. 544/337
4,298,602 11/1981 Pawloski .......................... 546/23

FOREIGN PATENT DOCUMENTS 2410911 11/1975 Fed. Rep. of Germany ...... 544/337
   6424  1/1978 Japan .
 103866  8/1979 Japan .
7048994  3/1982 Japan ................................. 546/21
1085340  9/1967 United Kingdom ................ 544/337

Primary Examiner—Donald G. Daus
Assistant Examiner—G. Hendricks
Attorney, Agent, or Firm—Parkhurst & Oliff

[57] ABSTRACT

Novel N-containing heterocyclic ring-substituted O-arylphosphate derivatives, the preparation thereof and insecticides acaricides and nematicides containing said derivatives are provided. The O-arylphosphate derivatives have the general formula:

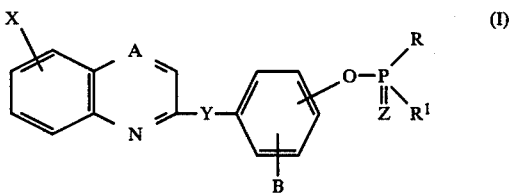

(I)

wherein A is —CH or nitrogen, X is hydrogen, a halogen or trifluoromethyl; Y is oxygen, S(O)n (wherein n is an integer of from 0 to 2) or $NR^2$ (wherein $R^2$ is hydrogen or a lower alkyl); Z is oxygen or sulfur; R and $R^1$ independently are a lower alkoxy or lower alkylthiol; and B is hydrogen, a halogen or a lower alkyl. The O-arylphosphate derivatives have an excellent insecticidal acaricidal and nematocidal action.

15 Claims, No Drawings

N-CONTAINING HETEROCYCLIC RING-SUBSTITUTED O-ARYLPHOSPHATE DERIVATIVES, PREPARATION THEREOF, AND INSECTICIDES, ACARICIDES AND NEMATOCIDES CONTAINING SAID DERIVATIVES

BACKGROUND OF THE INVENTION (1) Field of the Invention

This invention relates to a novel N-containing heterocyclic ring-substituted O-arylphosphate derivative, a process for preparation thereof, and an insecticide, acaricide and nematicide (hereinafter referred to as "insecticide) containing said derivative as an active ingredient.

(2) Description of the Prior Art

Hitherto, a variety of insecticides have been developed and put into practice, and some of these insecticides have contributed to increase the productivity of agricultural and horticultural crops.

Pyridine-substituted O-arylphosphate derivatives have been known (see U.S. Pat. No. 4,080,443 and Japanese Patent Laid-Open Pub. No. 6424/78). The pyridine-based phosphate derivatives have been found unsatisfactory with respect to insecticidal action and the like.

Thus, novel insecticides having higher insecticidal activity are now desired in this field.

The present inventors have made intensive researches on insecticidal activities of many heterocyclic compounds in order to develop novel and useful insecticides and have unexpectedly found that novel O-arylphosphate derivatives having a quinolyl or quinoxalyl group as the heterocyclic ring exhibit excellent insecticidal actions.

The O-arylphosphate derivatives having a quinolyl or quinoxalyl group are novel compounds, which have not yet been disclosed in literature and have been prepared for the first time by the present inventors so far as they know.

SUMMARY OF THE INVENTION

An object of this invention is to provide novel O-arylphosphate derivatives which have an N-containing heterocyclic ring in their structure and exhibit excellent insecticidal activities.

Another object of this invention is to provide a process for preparing novel O-arylphosphate derivatives having an N-containing heterocyclic ring.

A further object of this invention is to provide novel and useful insecticides.

Other objects of this invention will be apparent from the description below.

DETAILED DESCRIPTION OF THE INVENTION

The compounds according to the invention have the general formula (I):

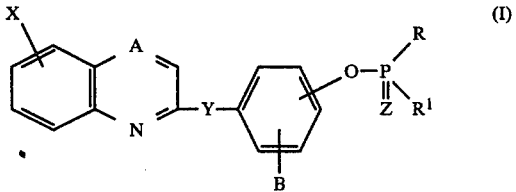

wherein A represents —CH or nitrogen; X represents hydrogen, a halogen or trifluoromethyl; Y represents oxygen, S(O)n (wherein n is an integer of from 0 to 2) or $NR^2$ (wherein $R^2$ is hydrogen or a lower alkyl); Z represents oxygen or sulfur; R and $R^1$ independently represent a lower alkoxy or lower alkylthio; and B represents hydrogen, a halogen or a lower alkyl.

Preferred $R^2$ as the lower alkyl is a straight or branched $C_1$-$C_4$ alkyl group, especially methyl.

The alkyl moiety in R or $R^1$ is preferably a straight or branched $C_1$-$C_4$ alkyl group such as methyl, ethyl, propyl or butyl, more preferably ethyl or propyl.

Preferred B as the lower alkyl is a straight or branched $C_1$-$C_4$ alkyl group, and more preferably methyl.

The halogen for X or B is preferably fluorine, chlorine or bromine.

Preferred compounds according to the invention have the general formula (IA):

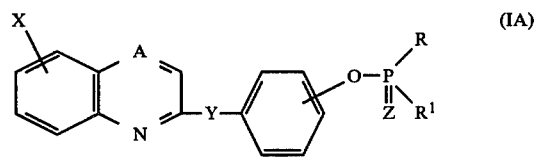

wherein X, A, Y, Z, R and $R^1$ have the same meanings as above, or the general formula (IB):

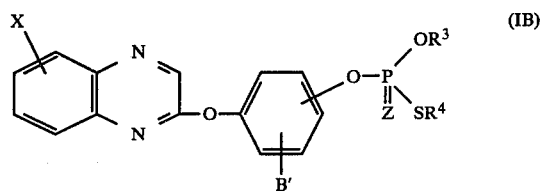

wherein X and Z have the same meanings as above; B' represents a halogen or a lower alkyl, and preferably a $C_1$-$C_4$ alkyl; and $R^3$ and $R^4$ independently represent a lower alkyl, preferably a $C_1$-$C_4$ alkyl.

Of the compounds of the formula (IA), more preferred are those having the general formula (IA)':

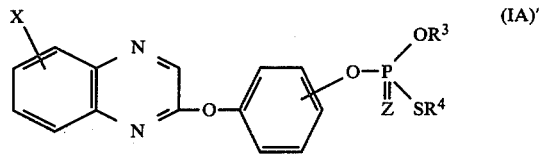

wherein X, Z, $R^3$ and $R^4$ have the same meanings as above.

Compounds of particular importance of the formula (IA)' are those wherein

X is hydrogen, chlorine, fluorine, bromine or trifluoromethyl;
Z is oxygen or sulfur, especially oxygen;
R³ is ethyl; and
R⁴ is a propyl, especially n-propyl.

The compounds of the formula (IA)' are exemplified by the following:

O-ethyl S-n-propyl O-[4-(quinoxalyl-2-oxy)phenyl]-thiophosphate,

O-ethyl S-n-propyl O-[3-(6-chloroquinoxalyl-2-oxy)-phenyl]thiophosphate,

O-ethyl S-n-propyl O-[4-(6-chloroquinoxalyl-2-oxy)-phenyl]thiophosphate,

O-ethyl S-n-propyl O-[2-(6-chloroquinoxalyl-2-oxy)-phenyl]thiophosphate,

O-ethyl S-n-propyl O-[4-(6-fluoroquinoxalyl-2-oxy)-phenyl]thiophosphate,

O-ethyl S-n-propyl O-[4-(6-trifluoromethylquinoxalyl-2-oxy)-phenyl]thiophosphate, O-ethyl S-n-propyl O-[4-(7-bromoquinoxalyl-2-oxy)-phenyl]thiophosphate.

Compounds of particular importance among the compounds of the formula (IB) are those wherein X is hydrogen, chlorine, bromine or trifluoromethyl;
B' is chlorine, bromine or methyl,
Z is oxygen or sulfur, especially oxygen;
R³ is ethyl, and
R⁴ is a propyl, especially n-propyl.

The compounds of the formula (IB) are exemplified by the following:

O-ethyl S-n-propyl O-[2-chloro-4-(7-bromoquinoxalyl-2-oxy)phenyl]thiophosphate,

O-ethyl S-n-propyl O-[2-bromo-4-(quinoxalyl-2-oxy)-phenyl]thiophosphate,

O-ethyl S-n-propyl O-[3-chloro-4-(7-bromoquinoxalyl-2-oxy)phenyl]thiophosphate,

O-ethyl S-n-propyl O-[2-methyl-4-(6-trifluoromethyl-quinoxalyl-2-oxy)phenyl]thiophosphate, O-ethyl S-n-propyl O-[2-bromo-4-(quinoxalyl-2-oxy)-phenyl]dithiophosphate, O-ethyl S-n-propyl O-[2 or 4-chloro-5-(6-chloroquinoxalyl-2-oxy)phenyl]thiophosphate, O-ethyl S-n-propyl O-[6-methyl-5-(6-chloroquinoxalyl-2-oxy)phenyl]thiophosphate.

Incidentally, by the term "N-containing heterocyclic ring-substituted O-arylphosphate derivatives" used herein is meant the compounds represented by the general formulae given above, or shown by the above-mentioned chemical names.

The compounds of the formula (I) may be generally synthesized according to the following reaction method;

-continued

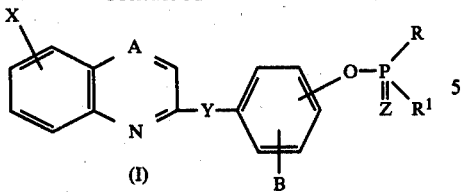
(I)

wherein A, X, Y, Z, R, R¹ and B have the same meanings as above.

Namely, the compounds of the formula (I) can be prepared by reacting monochloride of a phosphate derivative of the formula (II) with a phenol derivative of the formula (III) in an organic solvent in the presence of an acid acceptor. The reaction time is usually 30 minutes to 5 hours, preferably 1 to 3 hour. The reaction temperature is usually in the range of from 5° to 60° C., preferably 30° to 50° C.

The organic solvent to be used may be benzene, acetonitrile, methyl ethyl ketone, chloroform, methylene chloride, dimethylsulfoxide and the like. The acid acceptor to be used may be triethylamine, pyridine, potassium carbonate, potassium t-butoxide and the like.

After completion of the reaction, the reaction mixture is poured into cold water and extracted with an appropriate organic solvent. The organic layer is washed with water and dried. The organic solvent is then distilled off to give a crude product. Purification of the resulting crude product by column chromatography, gives a substantially pure compound of the formula (I).

The monochlorides of phosphate derivative of the formula (II) are known compounds and can be prepared by known methods. For example, an O,S-dialkylphosphorochloride thiolate (i.e. a compound of the formula (II), wherein R is a lower alkoxy, R¹ is a lower alkylthio and Z is oxygen) can be synthesized by the method disclosed in Japanese Patent Publication No. 86/1977 and German Patent Publication No. 2635931. Moreover, an O,S-dialkylphosphorochloride dithiolate (i.e. a compound of the formula (II), wherein R is a lower alkoxy, R¹ is a lower alkylthio and Z is sulfur) can be synthesized by the method disclosed in Japanese Patent Laid Open Publication No. 125127/77.

The phenol derivatives of the formula (III) wherein Y is oxygen can be synthesized by the method similar to that disclosed in Japanese Patent Laid Open Publication No. 51454/81. Also, the phenol derivatives of the formula (III) wherein Y is NR² can be prepared by the method similar to that of Japanese Patent Laid Open Publication No. 57770/81. Synthesis of the phenol derivatives of the formula (III) wherein Y is S(O)n will be described below in Synthesis Example 3.

The compound of the formula (I) wherein B is hydrogen, and one of R and R¹ is a lower alkoxy and the other is a lower alkylthio may also be synthesized through the following reaction scheme:

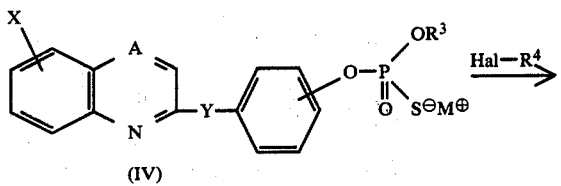
(IV)

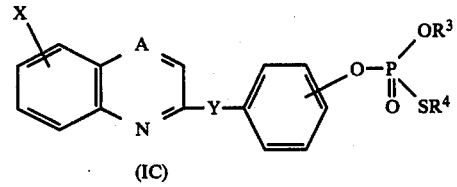
(IC)

wherein A, X and Y have the same meanings as above; Hal represents a halogen atom such as chlorine, bromine and iodine; M represents an alkali metal such as potassium and sodium; and R³ and R⁴ have the same meaning as defined for formula (IB). Namely, the compound of the formula (IC) can be obtained in a good yield by reacting a thiophosphate salt of the formula (IV) with an appropriate lower alkyl halide.

The compounds of the present invention thus obtained are exceedingly useful as agents for controlling and combating sanitary insect pests as well as agricultural and horticultural insect pests which damage paddy-rice plants, vegetables, fruit trees, cotton plants and other crops and flowering plants, insect pests of forest and insect pests in stored crops.

In accordance with the present invention are provided insect pests-combating agents which are suitable to apply an effective amount of the present compounds onto the locus of insect pests.

The locus of insect pests herein means any place which insect pests inhabit, and includes, for example, soil, atmosphere, water, food, plants, fertilizers, inactive materials, and stored good such as cereals.

Typical pests to which the compounds of the present invention are applicable are exemplified in the following, but the application of the present invention is not restricted to these pests, or merely to insect pests, as shown in Test Example 5 (acaricidal action on mites) and Test Example 6 (nematicidal action on nematodes).

Sanitary insect pests:
  housefly (Musca domestica), mosquito (Culex spp., Aedes spp., Anopheles spp.) cockroach (Periplaneta spp., Blattella spp.)

Agricultural and horticultural insect pests:
(Insect pests of rice)
  rice stem borer (Chilo suppressalis),
  rice leaf beetle (Oulema oryzae),
  ricewater weevil (Lissothoptrus oryzophilus),
  rice leaf miner (Agromyza oryzae),
  smaller rice leaf miner (Hydrellia griseola),
  small brown planthopper (Laodelphax striatellus),
  white-backed rice planthopper (Sogatella furcifera),
  brown rice planthopper (Nilaparvata lugens),
  green rice leafhopper (Nephotettix cincticeps)

(Vegetable pests)
  cabbage armyworm (Mamestra brassicae),
  tobacco cutworm (Spodoptera litura),
  common white (Pieris rapae crucivora),
  diamondback moth (Plutella xylostella),
  28-spotted lady bettle (Epilachna vigintioctopunctata),
  Green peach aphid (Myzus persicae)
  Root-knot nematode (Meloidogyne sp.)
  Root-lesion nematode (Pratylenchus sp.)

(Insect pest of fruit tree)
  tortrix, Leafrolles (Adoxophyes spp., Archips spp., Archippus spp.),
  apple leafminer (Phyllonorycter ringoneella),
  oriental fruit moth (Grapholita molesta), peach fruit moth (*Carposina niponensis*),
smaller tea tortrix (*Adoxophyes orana*),
comstock mealybug (*Pseudococcus comstocki*)

Generally, it is preferred that the insecticides according to the present invention are applied in a concentration of 0.1 to 10,000 ppm, especially 0.5 to 2,000 ppm, of an active substance. In the case of aquatic insect pests, a liquid insecticide containing an active substance within the above concentration range can be applied onto the breeding locus for controlling such pests: the insecticidal action is still effective with the concentration of the active substance in water outside of the above concentration range.

In applying the compounds of the present invention as insecticides, they are generally mixed with suitable carriers such as solid carriers, e.g. clay, talcum, bentonite, kaolin, bolus, loess, chalk, limestone, ground limestone, attaclay, dolomite, diatomaceous earth, precipitated silica, alkaline earth silicates, sodium and potassium aluminium silicates (feldspar and mica), secondary calcium phosphate, calcium and magnesium sulphates, magnesium oxide, ground synthetic materials etc.; or liquid carriers, e.g. water, alcohols (methanol, ethanol, etc.), ketones, ethers, aliphatic hydrocarbons, aromatic hydrocarbons (benzene, toluene, xylene, etc.,), organic bases, acid amides (dimethyl formamide, etc.), esters, nitriles, etc. If desired, the resulting mixture may be further supplemented with agents such as emulsifiers, dispersing agents, suspending agents, spread, penetrating agents and stabilizers to provide practical preparations such as emulsions, oil solutions, wettable powders, dusts, granules, pastes, flowables, aerosols, smoking chemicals, mosquito-repellent incenses, electric mosquito-repellent and the like.

Furthermore, it is possible to apply the insecticides of the present invention mixed or together with other insecticides, fungicides, herbicides, plant-controlling agents, fertilizers and the like in the course of preparation or application, if necessary.

The insecticidal action of the compounds according to the present invention can be further enhanced by adding thereto synergists such as piperonyl butoxide, octachlorodipropyl ether, N-octylbicycloheptene dicarboxyimide.

It is also possible to increase the stability of the compounds according to the present invention by adding thereto as an antioxidant phenolic compounds such as 2,6-di-tert.-butyl-4-methylphenol, 2,6-di-tert.-butylphenol, amine compounds, or the like.

The present invention will be further explained in detail by way of the following synthesis examples, formulation examples and test examples. It should be noted, however, that the present invention is not restricted to these illustrative examples.

SYNTHESIS EXAMPLE 1

O,O-diethyl-O-[4-(6-fluoroquinolyl-2-oxy)phenyl]-thiophosphate (Compound No. 1)

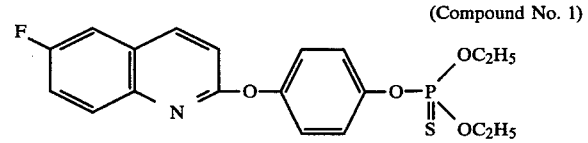

In 20 ml of dimethylsulfoxide is dissolved 4-(6-fluoroquinolyl-2-oxy)phenol (1.3 g), followed by addition thereto under cooling of potassium t-butoxide (0.7 g) all at once. Then, O,O-diethylthiophosphoryl chloride (1.0 g) is added dropwise to the reaction liquid under cooling. After the dropwise addition, the resulting reaction liquid is allowed to stand at room temperature for 5 minutes and then diluted with a large amount of water to terminate the reaction.

The reaction mixture is extracted with chloroform. The resulting chloroform phase is separated, washed with water, dried over anhydrous sodium sulfate, and then concentrated under reduced pressure to give a substantially pure product. The resulting product is subjected to purification by means of column chromatography to obtain 1.8 g of the aimed Compound No. 1 of the present invention as pale yellow liquid. $N_D^{20} = 1.5798$.

SYNTHESIS EXAMPLE 2

O-ethyl S-n-propyl O-[4-(6-fluoroquinoxalyl-2-oxy)-phenyl]thiophosphate (Compound No. 8)

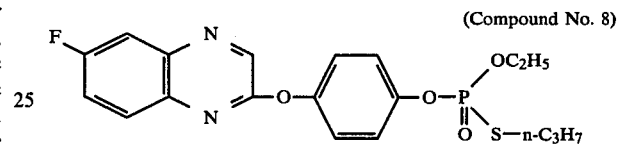

To 100 ml of chloroform are added 4-(6-fluoroquinoxalyl-2-oxy)phenyl (1.0 g), O-ethyl S-n-propyl thiophosphoryl chloride (0.7 g) and triethylamine (0.4 g), and the resulting solution is heated under reflux for 7 hours. The resulting reaction liquid is washed with water, dried and concentrated under reduced pressure to give pale red oily residue. The resulting oily residue is subjected to purification by means of column chromatography to obtain 0.8 g of the compound No. 8 of the present invention as a yellow oil. $N_D^{20} = 1.5779$

SYNTHESIS EXAMPLE 3

O-ethyl S-n-propyl O-[4-(7-bromoquinoxalyl-2-thio)-phenyl]dithiophosphate (Compound No. 20)

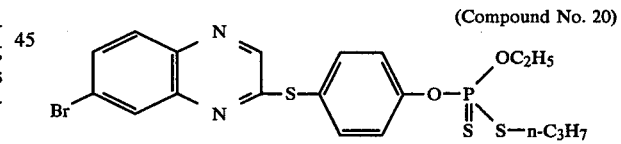

In 300 ml of methylene chloride is dissolved 4-(7-bromoquinoxalyl-2-thio)anisole (12 g), followed by addition thereto under cooling to $-78°$ C. of boron tribromide (25 g). Thereafter, the resulting reaction liquid is gradually warmed to room temperature, allowed to stand at room temperature for 3 days and then diluted carefully with water to terminate the reaction. The methylene chloride phase is mixed with 5% NaOH aqueous solution and the aqueous alkaline phase separated therefrom is slightly acidified with diluted hydrochloric acid to precipitate pale yellow solid. The resulting pale yellow crystals are sufficiently dehydrated and dried to obtain 7.6 g of substantially pure 4-(7-bromoquinoxalyl-2-thio)phenol. (m.p. 191°–194° C.)

In 50 ml of chloroform are dissolved the phenol obtained in the above (1.3 g), O-ethyl S-n-propyl dithiophosphoryl chloride (1.1 g) and triethylamine (0.6 g) and the resulting chloroform solution is heated under reflux for 7 hours. The chloroform reaction liquid is then washed with diluted alkaline aqueous solution and then with water, dried and concentrated under reduced pressure to give substantially pure compound No. 20 of the present invention as a pale yellow oil. The resulting product is subjected to purification by column chromatography to obtain 1.1 g of pure compound No. 20 of the present invention as a pale yellow oil. $N_D^{20} = 1.6675$

SYNTHESIS EXAMPLE 4

O-ethyl S-n-propyl O-[3-(6-chloroquinoxalyl-2-oxy)-phenyl]thiophosphate (Compound No. 22)

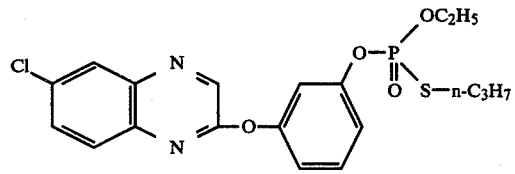

A solution of 3-(6-chloroquinoxalyl-2-oxy)phenol (1.5 g), O-ethyl-S-n-propylthiophosphoryl chloride (1.0 g) and triethylamine (0.6 g) in 100 ml of methylene chloride is heated under reflux for 5 hrs. The reaction mixtures is then washed with water, dried and concentrated to give pale red, oily residue. The oily residue is purified by means of silica gel column chromatography to obtain 1.1 g of substantially pure compound No. 22 of the present invention. $N_D^{20} = 1.5963$ In the manner similar to Synthesis Examples 1 to 4, the compounds listed in Tables 1, 2 and 3 were synthesized. The physical properties of these compounds are also listed in the tables together with those of compounds No. 1, 20 and 22.

TABLE 1

Syntheses of the compounds of the formula (Ia):

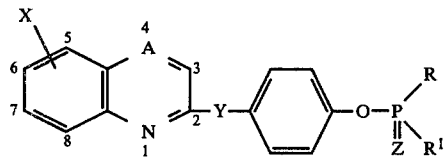

(Ia)

| Compound No. | X | Y | Z | A | R | R¹ | Appearance | $N_D^{20}$ |
|---|---|---|---|---|---|---|---|---|
| 1 | 6-F | O | S | CH | $OC_2H_5$ | $OC_2H_5$ | pale yellow liquid | 1.5798 |
| 2 | H | O | O | CH | SPr—n* | $OC_2H_5$ | pale yellow liquid | 1.5790 |
| 3 | 6-F | O | O | CH | SPr—n | $OC_2H_5$ | pale yellow liquid | 1.5769 |
| 4 | 6-Br | O | O | CH | SPr—n | $OC_2H_5$ | pale yellow liquid | 1.6093 |
| 5 | 6-Cl | O | S | N | $OC_2H_5$ | $OC_2H_5$ | pale yellow liquid | 1.5909 |
| 6 | 6-F | O | S | N | $OC_2H_5$ | $OC_2H_5$ | pale yellow liquid | 1.5629 |
| 7 | H | O | O | N | SPr—n | $OC_2H_5$ | pale yellow liquid | 1.5542 |
| 8 | 6-F | O | O | N | SPr—n | $OC_2H_5$ | pale yellow liquid | 1.5779 |
| 9 | 6-Cl | O | O | N | SPr—n | $OC_2H_5$ | pale yellow liquid | 1.5729 |
| 10 | 6-$CF_3$ | O | O | N | SPr—n | $OC_2H_5$ | pale yellow liquid | 1.5506 |
| 11 | 7-Br | O | O | N | SPr—n | $OC_2H_5$ | pale yellow liquid | 1.6000 |
| 12 | 6-Cl | $NCH_3$ | O | N | SPr—n | $OC_2H_5$ | pale yellow liquid | 1.6048 |
| 13 | 6-Cl | S | O | N | SPr—n | $OC_2H_5$ | pale yellow liquid | 1.6298 |
| 14 | 6-F | O | S | N | SPr—n | $OC_2H_5$ | pale yellow liquid | 1.6008 |
| 15 | 6-Cl | O | S | N | SPr—n | $OC_2H_5$ | pale yellow liquid | 1.6222 |
| 16 | 6-Cl | O | O | N | SPr—n | $OCH_3$ | pale yellow liquid | |
| 17 | H | O | S | N | SPr—n | $OC_2H_5$ | pale yellow liquid | 1.6168 |
| 18 | 7-Br | O | O | N | SPr—n | $OCH_3$ | pale yellow liquid | |
| 19 | 7-Br | S | O | N | SPr—n | $OC_2H_5$ | pale yellow liquid | 1.6349 |
| 20 | 7-Br | S | S | N | SPr—n | $OC_2H_5$ | pale yellow liquid | 1.6675 |
| 21 | 6-Cl | $NCH_3$ | S | N | SPr—n | $OC_2H_5$ | pale yellow liquid | Viscous liquid |

*"SPr—n" herein represents S—n-propyl group.

TABLE 2
Syntheses of the compounds of the formula (Ib):

(Ib) structure shown

| Compound No. | X | Y | Z | A | R | $R^1$ | Appearance | $N_D^{20}$ |
|---|---|---|---|---|---|---|---|---|
| 22 | 6-Cl | O | O | N | SPr—n | $OC_2H_5$ | pale yellow liquid | 1.5963 |
| 23 | 7-Br | O | O | N | SPr—n | $OC_2H_5$ | pale yellow liquid | 1.5765 |
| 24 | 6-Cl | O | S | N | SPr—n | $OC_2H_5$ | pale yellow liquid | 1.6302 |

TABLE 3
Syntheses of the compounds of the formula (Ic):

(Ic) structure shown

| Compound No. | X | Y | Z | A | R | $R^1$ | Appearance | $N_D^{20}$ |
|---|---|---|---|---|---|---|---|---|
| 25 | H | O | O | N | SPr—n | $OC_2H_5$ | pale yellow liquid | 1.5936 |
| 26 | 7-Br | O | O | N | SPr—n | $OC_2H_5$ | pale yellow liquid | 1.6042 |
| 27 | 6-CF$_3$ | O | O | N | SPr—n | $OC_2H_5$ | pale yellow liquid | 1.5519 |
| 28 | 6-F | O | O | N | Spr—n | $OC_2H_5$ | pale yellow liquid | 1.5753 |
| 29 | 6-Cl | O | O | N | SPr—n | $OC_2H_5$ | pale yellow liquid | 1.5968 |
| 30 | 6-Cl | O | S | N | SPr—n | $OC_2H_5$ | pale yellow liquid | 1.6178 |

SYNTHESIS EXAMPLE 5

O-ethyl S-n-propyl O-[2-chloro-4-(7-bromoquinoxalyl-2-oxy)phenyl]thiophosphate (Compound No. 33)

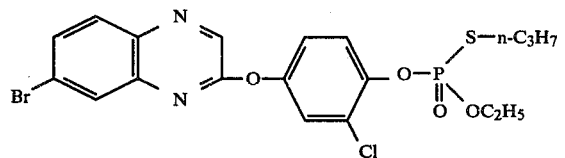

In 50 ml of chloroform are dissolved 2-chloro-4-(7-bromoquinoxalyl-2-oxy)phenol (1.0 g), O-ethyl S-n-propyl thiophosphoryl chloride (0.86 g) and triethylamine (0.43 g), and the resulting solution is heated under reflux for 20 hours.

The reaction liquid is washed with 5% NaOH aqueous solution then with water, dried and concentrated to give yellow, oily residue. The resulting oily residue is subjected to purification by means of column chromatography to yield 0.57 g of compound No. 33 of the present invention as a pale yellow liquid. $N_D^{20}=1.6062$ In the same manner as the above example, the compounds listed in Table 4 were synthesized.

TABLE 4
Syntheses of the compounds of the formula (Id):

(Id) structure shown

| Compound No. | X | B | Z | R | $R^1$ | $N_D^{20}$ |
|---|---|---|---|---|---|---|
| 32 | H | 2-Br | O | SPr—n | $OC_2H_5$ | 1.5891 |
| 33 | 7-Br | 2-Cl | O | SPr—n | $OC_2H_5$ | 1.6062 |
| 34 | 7-Br | 3-Cl | O | SPr—n | $OC_2H_5$ | 1.5969 |
| 35 | 6-CF$_3$ | 2-CH$_3$ | O | SPr—n | $OC_2H_5$ | 1.5564 |
| 36 | H | 2-Br | S | SPr—n | $OC_2H_5$ | 1.6242 |

SYNTHESIS EXAMPLE 6

O-ethyl S-n-propyl O-[2-chloro-5-(6-chloroquinoxalyl-2-oxy)phenyl]thiophosphate (Compound No. 37)

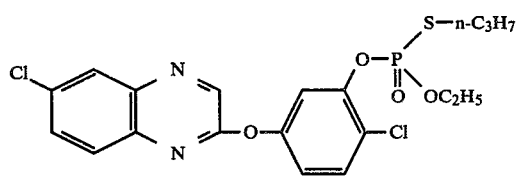

A mixture of 2,6-dichloroquinoxaline (6.0 g), 4-chlororesorcinol (12.6 g), anhydrous potassium carbonate (8.4 g) and dimethyl formamide (30 g) is reacted with stirring at 110° C. for 4 hours. After completion of the reaction, dimethyl formamide in the reaction mixture is distilled off under reduced pressure and the resulting residue is added with water to precipitate crystals.

The crystals thus obtained are filtered, washed with water and dried. The resulting crude product is subjected to purification by means of column chromatography to obtain 1.3 g of white crystals of 4-chloro-3-(6-chloroquinoxalyl-2-oxy)phenol in the first eluate (m.p. 195°–199° C.), and as the second eluate 1.0 g of white crystals of 2-chloro-5-(6-chloroquinoxalyl-2-oxy)phenol. (m.p. 172°–176° C.).

In 50 ml of chloroform are added 2-chloro-5-(6-chloroquinoxalyl-2-oxy)phenol (0.90 g), O-ethyl S-n-propyl thiophosphoryl chloride (0.89 g) and triethylamine (0.45 g), and the resulting solution is heat under reflux for 24 hrs.

The reaction liquid is subjected to post-treatment as in Synthesis Example 5 to obtain 0.73 g of pure compound No. 37 as a pale yellow liquid. $N_D^{20}=1.5982$ In the manner similar to that of Synthesis Example 6, the compounds listed in Table 5 were synthesized.

TABLE 5
Syntheses of the compounds of the formula (Ie):

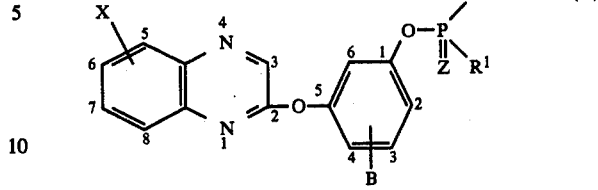

(Ie)

| Compound No. | X | B | Z | R | R¹ | $N_D^{20}$ |
|---|---|---|---|---|---|---|
| 38 | 6-Cl | 4-Cl | O | SPr—n | OC₂H₅ | 1.6025 |
| 39 | 6-Cl | 6-CH₃ | O | SPr—n | OC₂H₅ | 1.5851 |

In the same manner as any of Synthesis Examples 1 to 6, the compounds listed in Tables 6 and 7 may be synthesized.

TABLE 6
Syntheses of the compounds of the formula (If):

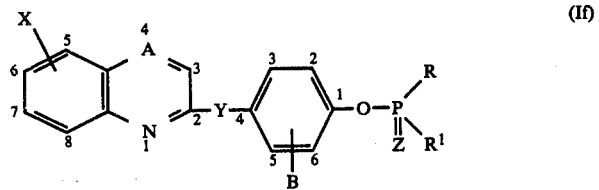

(If)

| Compound No. | X | Y | Z | A | B | R | R¹ |
|---|---|---|---|---|---|---|---|
| 40 | H | O | O | CH | H | SPr—n | OCH₃ |
| 41 | H | O | O | CH | H | SBu—n** | OC₂H₅ |
| 42 | H | O | O | CH | H | SBu—sec*** | OC₂H₅ |
| 43 | H | O | O | CH | 2-Br | SPr—n | OC₂H₅ |
| 44 | H | O | O | CH | 2-Cl | SPr—n | OC₂H₅ |
| 45 | 6-F | O | O | CH | H | SPr—n | OCH₃ |
| 46 | 6-F | O | O | CH | H | SBu—n | OC₂H₅ |
| 47 | 6-F | O | O | CH | H | SBu—sec | OC₂H₅ |
| 48 | 6-F | O | O | CH | 2-Br | SPr—n | OC₂H₅ |
| 49 | 6-F | O | O | CH | 2-Cl | SPr—n | OC₂H₅ |
| 50 | 6-Br | O | O | CH | H | SBu—sec | OC₂H₅ |
| 51 | H | O | O | N | H | SPr—n | OCH₃ |
| 52 | H | O | O | N | H | SBu—n | OC₂H₅ |
| 53 | H | O | O | N | H | SBu—sec | OC₂H₅ |
| 54 | H | O | O | N | 2-Br | SPr—n | OCH₃ |
| 55 | H | O | O | N | 2-Br | SBu—n | OC₂H₅ |
| 56 | H | O | O | N | 2-Br | SBu—sec | OC₂H₅ |
| 57 | H | O | O | N | 2-Cl | SPr—n | OC₂H₅ |
| 58 | H | O | O | N | 3-Cl | SPr—n | OC₂H₅ |
| 59 | H | NH | O | N | H | SPr—n | OC₂H₅ |
| 60 | H | NC₂H₅ | O | N | H | SPr—n | OC₂H₅ |
| 61 | H | SO | O | N | H | SPr—n | OC₂H₅ |
| 62 | H | SO₂ | O | N | H | SPr—n | OC₂H₅ |
| 63 | 6-Cl | O | O | N | H | SPr—n | OCH₃ |
| 64 | 6-Cl | O | O | N | H | SPr—n | OPr—n**** |
| 65 | 6-Cl | O | O | N | H | SBu—n | OC₂H₅ |
| 66 | 6-Cl | O | O | N | H | SBu—sec | OC₂H₅ |
| 67 | 6-Cl | O | O | N | 2-Br | SPr—n | OC₂H₅ |
| 68 | 6-Cl | O | O | N | 2-Br | SBu—sec | OC₂H₅ |
| 69 | 6-Cl | O | O | N | 2-Cl | SPr—n | OC₂H₅ |
| 70 | 6-Cl | O | O | N | 2-Cl | SBu—sec | OC₂H₅ |
| 71 | 6-Cl | O | O | N | 3-Cl | SPr—n | OC₂H₅ |
| 72 | 6-Cl | O | O | N | 2-CH₃ | SPr—n | OC₂H₅ |
| 73 | 6-Cl | O | O | N | 3-CH₃ | SPr—n | OC₂H₅ |
| 74 | 6-Cl | NH | O | N | H | SPr—n | OC₂H₅ |
| 75 | 6-Cl | NC₂H₅ | O | N | H | SPr—n | OC₂H₅ |
| 76 | 6-Cl | SO | O | N | H | SPr—n | OC₂H₅ |
| 77 | 6-Cl | SO₂ | O | N | H | SPr—n | OC₂H₅ |
| 78 | 6-F | O | O | N | H | SPr—n | OCH₃ |
| 79 | 6-F | O | O | N | H | SPr—n | OPr—n |
| 80 | 6-F | O | O | N | H | SBu—n | OC₂H₅ |
| 81 | 6-F | O | O | N | H | SBu—sec | OC₂H₅ |

TABLE 6-continued
Syntheses of the compounds of the formula (If):

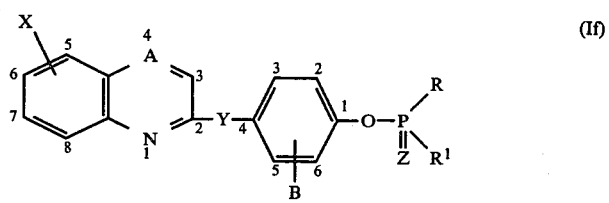

| Compound No. | X | Y | Z | A | B | R | R¹ |
|---|---|---|---|---|---|---|---|
| 82 | 6-F | O | O | N | 2-Cl | SPr—n | $OC_2H_5$ |
| 83 | 6-F | O | O | N | 3-Cl | SPr—n | $OC_2H_5$ |
| 84 | 6-F | $NCH_3$ | O | N | H | SPr—n | $OC_2H_5$ |
| 85 | 6-F | S | O | N | H | SPr—n | $OC_2H_5$ |
| 86 | 6-$CF_3$ | O | O | N | H | SPr—n | $OCH_3$ |
| 87 | 6-$CF_3$ | O | O | N | H | SBu—n | $OC_2H_5$ |
| 88 | 6-$CF_3$ | O | O | N | H | SBu—sec | $OC_2H_5$ |
| 89 | 6-$CF_3$ | O | O | N | 2-Br | SPr—n | $OC_2H_5$ |
| 90 | 6-$CF_3$ | O | O | N | 2-Cl | SPr—n | $OC_2H_5$ |
| 91 | 6-$CF_3$ | O | O | N | 3-Cl | SPr—n | $OC_2H_5$ |
| 92 | 6-$CF_3$ | NH | O | N | H | SPr—n | $OC_2H_5$ |
| 93 | 6-$CF_3$ | $NCH_3$ | O | N | H | SPr—n | $OC_2H_5$ |
| 94 | 6-$CF_3$ | $NC_2H_5$ | O | N | H | SPr—n | $OC_2H_5$ |
| 95 | 6-$CF_3$ | S | O | N | H | SPr—n | $OC_2H_5$ |
| 96 | 6-$CF_3$ | $SO_2$ | O | N | H | SPr—n | $OC_2H_5$ |
| 97 | 7-Br | O | O | N | H | SPr—n | $OCH_3$ |
| 98 | 7-Br | O | O | N | H | SBu—sec | $OC_2H_5$ |
| 99 | 7-Br | O | O | N | 2-Br | SPr—n | $OC_2H_5$ |
| 100 | 6-Cl | O | S | N | 2-Cl | SPr—n | $OC_2H_5$ |
| 101 | 6-Cl | O | S | N | 3-Cl | SPr—n | $OC_2H_5$ |

TABLE 7
Syntheses of the compounds of the formula (Ig):

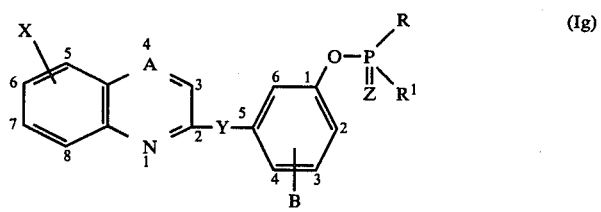

| Compound No. | X | Y | Z | A | B | R | R¹ |
|---|---|---|---|---|---|---|---|
| 102 | H | O | O | N | H | SPr—n | $OC_2H_5$ |
| 103 | H | O | O | N | H | SBu—sec*** | $OC_2H_5$ |
| 104 | H | O | O | N | 2-Cl | SPr—n | $OC_2H_5$ |
| 105 | H | O | O | N | 4-Cl | SPr—n | $OC_2H_5$ |
| 106 | H | O | O | N | 6-$CH_3$ | SPr—n | $OC_2H_5$ |
| 107 | 6-F | O | O | N | H | SPr—n | $OC_2H_5$ |
| 108 | 6-F | O | O | N | 2-Cl | SPr—n | $OC_2H_5$ |
| 109 | 6-F | O | O | N | 4-Cl | SPr—n | $OC_2H_5$ |
| 110 | 6-F | O | O | N | 6-$CH_3$ | SPr—n | $OC_2H_5$ |
| 111 | 6-Cl | S | O | N | H | SPr—n | $OC_2H_5$ |
| 112 | 6-Cl | O | O | N | H | SPr—n | OPr—n**** |
| 113 | 6-Cl | O | O | N | H | SBu—n** | $OC_2H_5$ |
| 114 | 6-Cl | O | O | N | H | SBu—sec | $OC_2H_5$ |
| 115 | 6-Cl | O | O | N | 4-Cl | SBu—n | $OC_2H_5$ |
| 116 | 6-Cl | O | O | N | 4-Cl | SBu—sec | $OC_2H_5$ |
| 117 | 6-Cl | $NCH_3$ | O | N | H | SPr—n | $OC_2H_5$ |
| 118 | 7-Br | O | O | N | H | S—Bu—sec | $OC_2H_5$ |
| 119 | 7-Br | O | O | N | 2-Cl | SPr—n | $OC_2H_5$ |
| 120 | 7-Br | O | O | N | 4-Cl | SPr—n | $OC_2H_5$ |
| 121 | 7-Br | S | O | N | H | SPr—n | $OC_2H_5$ |
| 122 | 6-$CF_3$ | O | O | N | H | SPr—n | $OC_2H_5$ |
| 123 | 6-$CF_3$ | O | O | N | 2-Cl | SPr—n | $OC_2H_5$ |
| 124 | 6-$CF_3$ | O | O | N | 4-Cl | SPr—n | $OC_2H_5$ |
| 125 | 6-$CF_3$ | O | O | N | 6-$CH_3$ | SPr—n | $OC_2H_5$ |
| 126 | 6-$CF_3$ | $NCH_3$ | O | N | H | SPr—n | $OC_2H_5$ |
| 127 | 6-Cl | O | S | N | 2-Cl | SPr—n | $OC_2H_5$ |
| 128 | 6-Cl | O | S | N | 4-Cl | SPr—n | $OC_2H_5$ |
| 129 | 6-Cl | O | S | N | 6-$CH_3$ | SPr—n | $OC_2H_5$ |

TABLE 7-continued
Syntheses of the compounds of the formula (Ig):

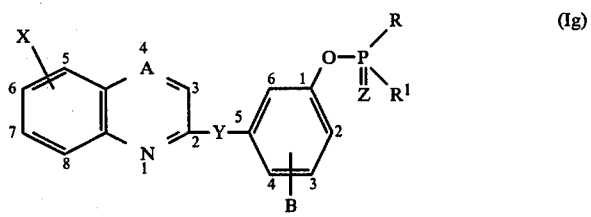

| Compound No. | X | Y | Z | A | B | R | R¹ |
|---|---|---|---|---|---|---|---|
| 130 | 6-Cl | O | S | N | 6-$C_2H_5$ | SPr—n | O$C_2H_5$ |

** "SBu—n" represents S—n-butyl group.
*** "SBu—sec" represents S—sec.-butyl group.
**** "OPr—n" represents O—n-propyl group.

In the following are indicated formulation examples in which the compounds of the present invention are used for insecticides. In these examples, all the parts mean parts by weight, if not otherwise specified.

Formulation Example 1: Emulsifiable concentrates
- an active substance (a compound according to the present invention)—5 parts
- xylol—80 parts
- Sorpol 2680 (trade name, supplied by Toho Chemicals Co., Ltd., Japan)—15 parts The above components are uniformly mixed to give an emulsifiable concentrate. The concentrate thus obtained is diluted with water either 50 times to spray the resulting emulsion in an amount of 25 to 50 ml/m² or 1000–2000 times to spray in an amount of 100 to 150 l/m².

Formulation Example 2: Oil solutions
- an active substance (a compound according to the present invention)—0.1 part
- piperonyl butoxide—0.9 part
- white kerosene—99.0 parts The above components are uniformly mixed to give an oily solution. The oily solution thus obtained is applied onto a drain or puddle in an amount of 25 to 50 ml/m².

Formulation Example 3: Wettable powders
- an active substance (a compound according to the present invention)—10 parts
- Siegreit (trade name, supplied by Siegreit Mining Industries Co., Ltd.,)—75 parts
- Carplex (trade name, supplied by Shionogi Seiyaku K.K., Japan)—10 parts
- Sorpol 8048 (trade name, supplied by Toho Chemicals, Co., Ltd., Japan)—3 parts
- Runox 1000 (trade name, supplied by Toho Chemicals, Co., Ltd., Japan)—2 parts The above components are uniformly mixed and ground to give an wettable powder. In application, the resulting wettable powder is diluted 100 to 2000 times with water and sprayed in an amount of 50 to 500 l/10a.

Formulation Example 4: Dusts
- an active substance (a compound according to the present invention)—0.4 part
- piperonyl butoxide—1.6 parts
- talcum—98 parts The above components are uniformly mixed to give a dust. The resulting dust is sprayed in an amount of about 15 g/m² or 3–4 kg/10a.

Formulation Example 5: Granules
- an active substance (a compound according to the present invention)—5 parts
- bentonite—95 parts The above components are uniformly mixed and ground. After addition of a small amount of water with sufficient stirring, the resulting mixture is granulated by means of an extruder granulator and dried to give granules. The granules thus obtained are directly sprayed in an amount of 3–12 kg/10a.

Excellent insecticidal actions of the compounds according to the present invention are explained below in comparison with that of the commercial product under generic name of "prothiophos", which contains active substance of the formula:

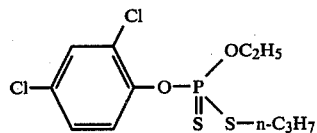

TEST EXAMPLE 1

Insecticidal action on house fly (Musca domestica) adult

One ml of acetone solution containing 100 ppm of the compound to be tested was added dropwise to a laboratory dish 9 cm in diameter so that the solution is evenly spread over the dish. After completely evaporating the acetone at room temperature, ten house fly adults were placed in the dish and then the dish was covered with a plastic cap provided with some pores. The dish containing the adults is placed in a thermostatic chamber kept at 25° C. An evaluation was made after 24 hours by counting the adults killed and calculating the mortality of adults in accordance with the following equation:

$$\text{Mortality} = \frac{\text{number of adults killed}}{\text{number of adults placed}} \times 100$$

The results thereof are listed in Table 8.
Incidentally, each test was repeated twice.

TABLE 8

| Test compound | Mortality (%) |
|---|---|
| Control (prothiophos) | 100 |
| Compound No. 2 | 100 |
| Compound No. 3 | 100 |

TABLE 8-continued

| Test compound | Mortality (%) |
| --- | --- |
| Compound No. 4 | 100 |
| Compound No. 5 | 80 |
| Compound No. 6 | 80 |
| Compound No. 7 | 100 |
| Compound No. 8 | 100 |
| Compound No. 9 | 100 |
| Compound No. 10 | 100 |
| Compound No. 11 | 100 |
| Compound No. 12 | 100 |
| Compound No. 13 | 100 |
| Compound No. 14 | 100 |
| Compound No. 15 | 100 |
| Compound No. 17 | 100 |
| Compound No. 19 | 100 |
| Compound No. 20 | 100 |
| Compound No. 21 | 100 |
| Compound No. 22 | 100 |
| Compound No. 23 | 100 |
| Compound No. 24 | 100 |
| Compound No. 25 | 100 |
| Compound No. 26 | 100 |
| Compound No. 27 | 100 |
| Compound No. 28 | 100 |
| Compound No. 29 | 100 |
| Compound No. 30 | 100 |
| Compound No. 32 | 100 |
| Compound No. 33 | 100 |
| Compound No. 34 | 100 |
| Compound No. 35 | 100 |
| Compound No. 36 | 100 |
| Compound No. 37 | 100 |
| Compound No. 38 | 100 |
| Compound No. 39 | 100 |

TEST EXAMPLE 2

Insecticidal action on green peach aphid (*Myzus persicae*)

Two ml of an aqueous emulsion containing 100 ppm of a compound according to the present invention was sprayed onto a laboratory dish of 3 cm in diameter charged with a leaf of cabbage infested with green peach aphids aphid. After spraying, the dish was fitted with a cap and stored in a thermostatic chamber kept at 25° C.

The mortality of the green peach aphids aphid in the dish was determined in the same manner as in Test Example 1 after 48 hours. The results are shown in Table 9.

TABLE 9

| Test compound | Mortality (%) |
| --- | --- |
| Control (prothiophos) | 100 |
| Compound No. 19 | 100 |
| Compound No. 25 | 100 |
| Compound No. 26 | 100 |
| Compound No. 27 | 100 |
| Compound No. 28 | 100 |
| Compound No. 29 | 100 |
| Compound No. 33 | 100 |
| Compound No. 34 | 100 |
| Compound No. 35 | 100 |
| Compound No. 37 | 100 |
| Compound No. 38 | 100 |
| Compound No. 39 | 100 |

TEST EXAMPLE 3

Contact insecticidal action on tobacco cutworm (*Spodoptera litura*) larvae

A leaf of cabbage was immersed in an aqueous emulsion containing 100 ppm of a compound according to the present invention for about 10 seconds, and then air-dried. The leaf thus treated was placed in a laboratory dish, into which 10 second inster tobacco cutworm larvae were released. The dish was fitted with a cap provided with some pores and then placed in a thermostatic chamber kept at 25° C. The mortality of the tobacco cutworm after 48 hours was determined in the same manner as in Test Example 1. The results thereof are shown in Table 10.

TABLE 10

| Test compound | Mortality (%) |
| --- | --- |
| Control (prothiophos) | 100 |
| Compound No. 2 | 100 |
| Compound No. 3 | 100 |
| Compound No. 4 | 100 |
| Compound No. 7 | 100 |
| Compound No. 8 | 100 |
| Compound No. 9 | 100 |
| Compound No. 10 | 100 |
| Compound No. 11 | 100 |
| Compound No. 12 | 100 |
| Compound No. 13 | 100 |
| Compound No. 14 | 100 |
| Compound No. 15 | 100 |
| Compound No. 17 | 100 |
| Compound No. 21 | 100 |
| Compound No. 22 | 100 |
| Compound No. 23 | 100 |
| Compound No. 24 | 100 |
| Compound No. 25 | 100 |
| Compound No. 28 | 100 |
| Compound No. 29 | 100 |
| Compound No. 30 | 100 |
| Compound No. 32 | 100 |
| Compound No. 33 | 100 |
| Compound No. 34 | 100 |
| Compound No. 36 | 100 |
| Compound No. 37 | 100 |
| Compound No. 38 | 100 |

TEST EXAMPLE 4

Insecticidal action on 28-spotted lady beetle (*Epilachna vigintioctopunctata*)

A piece of potato was immersed in an aqueous emulsion containing 100 ppm of a compound according to the present invention and then air-dried. The potato thus treated was placed in a laboratory dish, into which 10 second inster 28-spotted lady beetle larvae were released. The resulting dish was fitted with a cap provided with pores and then placed in a thermostatic chamber kept at 25° C. The number of the larvae killed was checked after 48 hours and the mortality thereof was determined in the same manner as Test Example 1.

Incidentally, the above test was repeated twice.

The test results are shown in Table 11.

TABLE 11

| Test compound | Mortality (%) |
| --- | --- |
| Control (prothiophos) | 0 |
| Compound No. 2 | 100 |
| Compound No. 3 | 100 |
| Compound No. 4 | 100 |
| Compound No. 7 | 100 |
| Compound No. 8 | 100 |
| Compound No. 9 | 100 |
| Compound No. 10 | 100 |
| Compound No. 11 | 100 |
| Compound No. 12 | 100 |
| Compound No. 13 | 100 |
| Compound No. 17 | 100 |
| Compound No. 19 | 100 |

TABLE 11-continued

| Test compound | Mortality (%) |
|---|---|
| Compound No. 22 | 100 |
| Compound No. 23 | 100 |
| Compound No. 24 | 100 |
| Compound No. 25 | 100 |
| Compound No. 26 | 100 |
| Compound No. 27 | 100 |
| Compound No. 28 | 100 |
| Compound No. 29 | 100 |
| Compound No. 30 | 100 |
| Compound No. 32 | 100 |
| Compound No. 33 | 100 |
| Compound No. 34 | 100 |
| Compound No. 35 | 100 |
| Compound No. 36 | 80 |
| Compound No. 37 | 100 |
| Compound No. 38 | 100 |
| Compound No. 39 | 100 |

TEST EXAMPLE 5

Acaricidal action on Kanzawa spider mite (*Tetranychus Kanzawai*)

A leaf of kidney bean was cut into a round piece of 1.5 cm in diameter by a leaf punch, and then placed on moistened filter paper put on a styrol cup of 7 cm in diameter. Each piece of the leaf was infested with 10 Kanzawa spider mite nympha. Half a day after the infestation, 2 ml of an aqueous emulsion containing 100 ppm of the active compound of the present invention was applied with a spreader to each styrol cup by means of a rotary sprinkler. The number of the nymphs killed was checked after 48 hours and the mortality of the nymphs was determined. The results are shown in Table 12.

TABLE 12

| Test compound | Mortality (%) |
|---|---|
| Control (prothiophos) | 100 |
| Compound No. 2 | 100 |
| Compound No. 3 | 100 |
| Compound No. 4 | 95 |
| Compound No. 7 | 100 |
| Compound No. 8 | 100 |
| Compound No. 9 | 100 |
| Compound No. 11 | 100 |
| Compound No. 13 | 95 |
| Compound No. 17 | 95 |
| Compound No. 19 | 100 |
| Compound No. 22 | 100 |
| Compound No. 23 | 100 |
| Compound No. 24 | 100 |
| Compound No. 25 | 100 |
| Compound No. 26 | 100 |
| Compound No. 27 | 100 |
| Compound No. 28 | 100 |
| Compound No. 29 | 100 |
| Compound No. 32 | 100 |
| Compound No. 33 | 100 |
| Compound No. 34 | 100 |
| Compound No. 35 | 100 |
| Compound No. 36 | 100 |
| Compound No. 37 | 100 |
| Compound No. 38 | 100 |
| Compound No. 39 | 100 |

TEST EXAMPLE 6

Nematocidal action on root-knot nematodes (Meloidogyne sp.)

Soil contaminated with root-knot nematodes was placed in a styrol cup of 8 cm in diameter. A liquid containing 100 ppm of an active substance was prepared by diluting an emulsifiable concentrate according to the present invention with water and adding a spreader thereto. The soil contaminated with nematodes and placed in the cup as described above was drenched with 50 ml of the resulting mixture. After 48 hours, a tomato seedling as an indicator is transplanted into the soil thus treated. 30 days after the transplantation, the roots of the tomato were washed with water and the root-knot parasitism was checked by observation. The results are shown in Table 13.

Rating of root-knot parasitism
- 0 ... no root-knot is observed at all.
- 1 ... a few root-knots are observed.
- 2 ... a medium number of root-knot is observed.
- 3 ... many root-knots are observed.
- 4 ... considerably many root-knots are observed.

TABLE 13

| Test compound | Root-knot parasitism rating |
|---|---|
| Control (prothiophos) | 0 |
| Compound No. 2 | 0 |
| Compound No. 3 | 0 |

| Test compound | Root-knot parasitism index |
|---|---|
| Compound No. 4 | 0 |
| Compound No. 7 | 0 |
| Compound No. 8 | 0 |
| Compound No. 9 | 0 |
| Compound No. 10 | 0 |
| Compound No. 11 | 1 |
| Compound No. 12 | 0 |
| Compound No. 13 | 1 |
| Compound No. 14 | 1 |
| Compound No. 15 | 1 |
| Compound No. 22 | 0 |
| Compound No. 23 | 1 |
| Compound No. 30 | 1 |
| Compound No. 32 | 0 |
| Compound No. 33 | 0 |
| Compound No. 34 | 0 |
| Compound No. 35 | 0 |
| Compound No. 36 | 0 |
| Compound No. 37 | 0 |
| Compound No. 38 | 0 |
| Compound No. 39 | 0 |

What we claim is:

1. An N-containing heterocyclic ring-substituted O-arylphosphate selected from the group consisting of the compounds of the formulae (IA)' and (IB):

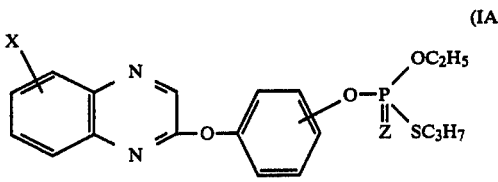

(IA)' and

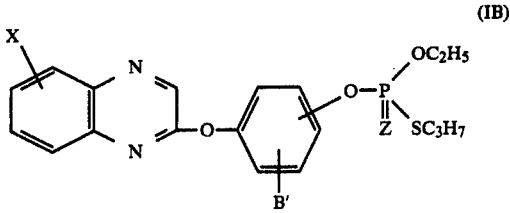

(IB)

wherein X represents hydrogen, a halogen or trifluoromethyl; Z represents oxygen or sulfur; and B' represents a halogen or a $C_1$–$C_4$ alkyl.

2. A compound according to claim 1, wherein Z in formula (IA)' or (IB) is oxygen.

3. A compound according to claim 2, wherein the —$SC_3H_7$ (S-propyl) is S-n-propyl.

4. A compound according to claim 2, wherein the compound is O-ethyl S-n-propyl O-[4-(quinoxalyl-2-oxy)phenyl]-thiophosphate.

5. A compound according to claim 2, wherein the compound is O-ethyl S-n-propyl O-[3-(6-chloroquinoxalyl-2-oxy)-phenyl]thiophosphate.

6. A compound according to claim 2, wherein the compound is O-ethyl S-n-propyl O-[4-(6-chloroquinoxalyl-2-oxy)-phenyl]thiophosphate.

7. A compound according to claim 2, wherein the compound is O-ethyl S-n-propyl O-[2-(6-chloroquinoxalyl-2-oxy)-phenyl]thiophosphate.

8. A compound according to claim 2, wherein the compound is O-ethyl S-n-propyl O-[4-(6-fluoroquinoxalyl-2-oxy)-phenyl]thiophosphate.

9. A compound according to claim 2, wherein the compound is O-ethyl S-n-propyl O-[4-(6-trifluoromethylquinoxalyl-2-oxy)pheny]thiophosphate.

10. A compound according to claim 2, wherein the compound is O-ethyl S-n-propyl O-[4-(7-bromoquinoxalyl-2-oxy)-phenyl]thiophosphate.

11. A compound according to claim 2, wherein the compound is O-ethyl S-n-propyl O-[2-chloro-5-(6-chloroquinoxalyl-2-oxy)phenyl]thiophosphate.

12. A compound according to claim 2, wherein the compound is O-ethyl S-n-propyl O-[4-chloro-5-(6-chloroquinoxalyl-2-oxy)phenyl]thiophosphate.

13. An insecticidal, acaricidal and nematocidal composition containing as an active ingredient an effective amount of at least one compound selected from the group consisting of the compounds of the formulae (IA)' and (IB):

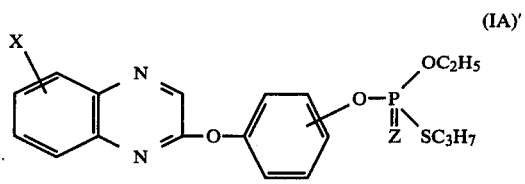

(IA)' and

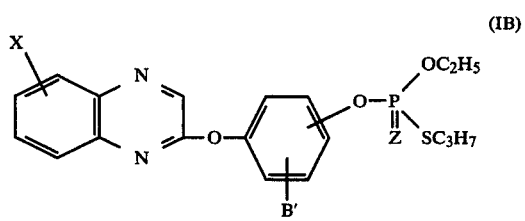

(IB)

wherein X represents hydrogen, a halogen or trifluoromethyl; Z represents oxygen or sulfur; and B' represents a halogen or a $C_1$–$C_4$ alkyl, together with a suitable carrier therefor.

14. An insecticidal, acaricidal and nematocidal composition according to claim 13, wherein Z in formula (IA)' or (IB) is oxygen.

15. An insecticidal, acaricidal and nematocidal composition according to claim 14, wherein the compound is selected from the group consisting of:

O-ethyl S-n-propyl O-[4-(quinoxalyl-2-oxy)-phenyl]-thiophosphate,

O-ethyl S-n-propyl O-[3-(6-chloroquinoxalyl-2-oxy)-phenyl]thiophosphate,

O-ethyl S-n-propyl O-[4-(6-chloroquinoxalyl-2-oxy)-phenyl]thiophosphate,

O-ethyl S-n-propyl O-[2-(6-chloroquinoxalyl-2-oxy)-phenyl]thiophosphate,

O-ethyl S-n-propyl O-[4-(6-fluoroquinoxalyl-2-oxy)-phenyl]thiophosphate,

O-ethyl S-n-propyl O-[4-(6-trifluoromethylquinoxalyl-2-oxy)phenyl]thiophosphate, O-ethyl S-n-propyl O-[4-(7-bromoquinoxalyl-2-oxy)-phenyl]thiophosphate, O-ethyl S-n-propyl O-[2-chloro-5-(6-chloroquinoxalyl-2-oxy)phenyl]thiophosphate, and O-ethyl S-n-propyl O-[4-chloro-5-(6-chloroquinoxalyl-2-oxy)phenyl]thiophosphate.

* * * * *